United States Patent [19]

Denton

[11] Patent Number: 4,837,031

[45] Date of Patent: Jun. 6, 1989

[54] COMPOSITIONS CONTAINING IBUPROFEN

[75] Inventor: Larry E. Denton, Collinsville, Ill.

[73] Assignee: Mallinckrodt, Inc., St. Louis, Mo.

[21] Appl. No.: 97,850

[22] Filed: Sep. 17, 1987

[51] Int. Cl.[4] ................................. A61K 9/14
[52] U.S. Cl. ..................... 424/464; 424/465; 424/490; 424/492; 424/494; 424/497
[58] Field of Search ............... 424/464, 465, 490, 492, 424/494, 497; 514/568

[56] References Cited

U.S. PATENT DOCUMENTS

| | | | |
|---|---|---|---|
| 4,036,948 | 7/1972 | Kitamori et al. | 424/492 |
| 4,439,453 | 3/1984 | Vogel | 424/494 |
| 4,555,399 | 11/1985 | Hsiao | 424/497 |
| 4,562,024 | 12/1985 | Rogerson | 514/562 |
| 4,609,675 | 9/1986 | Franz | 514/568 |
| 4,661,521 | 4/1987 | Salpekar et al. | 514/613 |

*Primary Examiner*—William R. Dixon, Jr.
*Assistant Examiner*—David M. Brunsman
*Attorney, Agent, or Firm*—Rogers, Howell, Moore & Haferkamp

[57] ABSTRACT

A granular composition containing 2-(4-isobutylphenyl)propionic acid (ibuprofen) as an active anti-inflammatory pharmaceutical ingredient as a major component, together with carboxymethylcellulose, a lubricant and water as minor components, is disclosed. Particles of ibuprofen and carboxymethylcellulose are both fluidized and coated with an aqueous disperson of a starch binder. After being dried to a moisture level of about 1–5% and blended with a lubricant and additional carboxymethylcellulose, the resulting granules can be directly molded into a pharmaceutically acceptable tablet having high hardness, short disintegration time and fast dissolution rate.

25 Claims, No Drawings

COMPOSITIONS CONTAINING IBUPROFEN

BACKGROUND OF THE INVENTION

1. Field of the Invention

The present invention relates to new and useful tabletable pharmaceutical compositions and methods of making the same. More particularly, the present invention relates to new and useful granular compositions containing ibuprofen which are eminently suitable for forming into tablets and methods for preparing such compositions using a fluidized bed apparatus.

2. Description of Prior Art

Ibuprofen, the generic name for 2-(4-isobutylphenyl)-propionic acid, is a well known anti-inflammatory drug and is disclosed in U.S. Pat. Nos. 3,228,831 and 3,385,886.

Normally, ibuprofen is formulated for sale to the consumer in the form of compressed tablets or capsules. U.S. Pat. No. 4,609,675 discloses a method of preparing a pharmaceutical ibuprofen-containing grauulate composition suitable for preparing tablets of relatively high dosage. This is accomplished by dry mixing ibuprofen with croscarmellose sodium NF (cross-linked sodium carboxymethylcellulose) in certain relative amounts, passing the resulting mixture through a roller compactor or slugging the composition and thereafter applying a size to the resulting compacted or slugged product.

Acetaminophen, the generic name for N-acetyl-p-aminophenol, is a well known analgesic drug and is disclosed in U.S. Pat. No. 2,998,450.

U.S. Pat. No. 4,661,521 discloses a method of preparing a pharmaceutical acetaminophen-containing granulate composition suitable for shaping into tablets. This is accomplished by using a fluid bed granulator-dryer involving spraying an aqueous slurry of a portion of a pregelatinized starch onto a fluidized composition of acetaminophen and thereafter drying the same. A lubricant may be added during or after drying.

Ibuprofen-containing granules having good compressibility properties to form tablets is a desideratum of long standing. Heretofore, when granules of ibuprofen are compressed to insure good crumbling resistance, the dissolution rate of the tablets is slower than desired.

SUMMARY OF THE INVENTION

Briefly, the present invention provides a new free-flowing pharmaceutical dry granules containing ibuprofen. The granules are suitable for directly shaping into tablets having excellent compressibility properties such that tablets compressed from the granules have good resistance to crumbling without significant sacrifice of the dissolution rate of the tablet.

The present invention also provides a method of preparing a free-flowing particulate composition capable of being directly formed into a tablet having high hardness, short disintegration time, and fast dissolution rate without being unacceptably friable.

The composition comprises as components thereof:

(a) the pharmaceutically active ingredient of ibuprofen in an amount of about 50 to 85 weight percent based on the total weight of the final composition, (b) the pharmaceutically acceptable cellulosic disintegrant of an internally cross-linked alkalai (sodium) carboxymethylcellulose in an effective amount of about 1-5 weight percent. Additionally, a pharmaceutically acceptable pregelatinized starch of about 10-25 weight percent and a microcrystalline cellulose of about 6-18 weight percent may be included along with carboxymethylcellulose as binders and disintegrants. The amount of disintegrants is sufficient to impart excellent dissolution and disintegration characteristics to tablets made therefrom, (c) optionally, the pharmaceutically acceptable binder of povidone in an amount of about 0.1-3.0 weight percent sufficient to impart suitable binding properties to tablets made from the composition, (d) a pharmaceutically acceptable lubricant in an effective amount of about 0.1-3.0 weight percent for imparting sufficient mold release properties to tablets made from the composition, and (e) water in an effective amount of about 1.0-5.0 weight percent.

The dosage of the ibuprofen active ingredient will normally range from about 100 to about 300 mg per tablet made from the composition of the present invention.

It is important that the arrangement of the ingredients of the compositions of the resulting granules be acheived by a fluid bed granulation-drying technique involving the steps of:

(a) charging the ibuprofen and a portion of the cellulosic disintegrant to a fluid bed granulator-dryer, (b) fluidizing the ibuprofen and cellulose disintegrant until thoroughly blended, (c) dispersing pregelatinized starch and water with a high sheer mixer to form a dispersion having from about 5 to about 15 weight percent solids, (d) spraying the starch dispersion onto the fluidized bed of active ingredient and cellulose disintegrant at a rate sufficient to maintain the fluidized bed moisture between 5 to about 20 percent by weight, (e) continuing drying after all the dispersion has been sprayed to reach a bed moisture of about 5 percent by weight or less, (f) stopping the fluidization, (g) transferring the dried product of the fluidization to a blender, (h) adding an lubricant to the blender, and (i) blending the lubricant onto the fluidized composition.

DETAILED DESCRIPTION OF THE INVENTION

The ibuprofen component is preferably provided in a powder or other finely divided form. The ibuprofen powder should be of high purity of greater than 99%. It has been found that when more than 30% by weight of the ibuprofen powder is larger than 60 mesh (U.S. Standard Siev(e), then the compressibility of the granules is adversely affected. For use in the present invention preferably all of the ibuprofen powder should pass through a 60 mesh screen, more preferably 95% will pass through an 100 mesh screen. The particle size of the ibuprofen powder is about 15-60 microns.

The internally cross-linked alkalai carboxymethylcellulose component of the directly tabletable composition of the present invention may be obtained from any well known manufacturer such as, for example, FMC Corporation of Philadelphia, Pennsylvania. Sodium carboxymethylcellulose is a cellulose ether produced by reacting alkali cellulose with sodium monochloroacetate under rigidly controlled conditions. This cellulosic material in solid pharmaceutical compositions aids in the dissolution rates and disintegration characteristics and must meet all of the NF requirements for such material.

The pregelatinized starch may be obtained from any well known manufacturer such as, for example, the National Starch Corporation. Pregelatinized starches useful in the present invention should meet all the NF requirements for such starches.

Povidone may be included as an optionally additional binder and is a polymer of vinylpyrrolidone and is produced commercially as a series of products having mean molecular weights ranging from about 10,000 to 700,000. Povidone is also readily available from various manufacturers as a pharmaceutical excipient.

The lubricant component may be any suitable pharmaceutically acceptable lubricant, which may be, e.g., hydrophilic or hydrophobic. This component is present in a lubricating amount at least sufficient to impart mold release properties to tablets formed from the compositions and preferably insufficient to increase disintegration and dissolution time of such tablets, and preferably insufficient to decrease the hardness of tablets formed from compositions of this invention containing lower lubricating amounts of the same lubricant.

Suitable lubricants for use as the lubricating component include, for example, stearic acid, metal stearates, such as sodium, calcium, magnesium and zinc stearate etc., sodium lauryl sulfate, polyethylene glycol, hydrogenated vegetable oils, talc and compressible mixtures of two or more such materials. Stearic acid and calcium stearate, singly or in combination, are preferred.

In general the lubricant may be present in an amount from about 0.1 to about 3.0 percent, more preferably from about 0.5 to 1.5 percent, and most preferably about 1 percent, based on the total dry weight of the composition.

The composition also includes water in an amount effective for aid in direct tablet formation. Such an effective amount is generally found to be between about 1.0 to 5.0 percent based on the total weight of the composition, preferably from about 2.3 to 3.3 percent on the same basis.

To increase the shelf life of the tablets, the composition may also contain an effective amount of a preservative. Suitable preservatives include methyl paraben which is the methyl ester of parahydroxybenzoic acid and propyl paraben which is the propyl ester of parahydroxybenzoic acid. Both of these esters are known substances for preventing microbial contamination. While the preservatives may be added during any stage in the preferred that any preservative be added during the spraying step.

Optionally, the composition may further include a pharmaceutically acceptable compressibility-promoting binder as an additional binding agent in the amount effective for increasing the obtainable hardness of tablets formed from the composition. Materials suitable for use as the optionally included binding agents include, for example, starch paste, polyvinylpyrrolidone, hydroxypropylmethylcellulose, hydroxypropylcellulose, gelatin, microcrystalline cellulose, natural gums, e.g., gum acacia, gum tragacanth, etc., sucrose, mannitol, ethylcellulose, synthetic polymer binders, used in the industry and compatible mixtures of two or more of the materials. Polyvinylpyrrolidone (PVP) is preferred (more preferably PVP ®K-90). In general, such an effective amount of optional binder is from about 0.5 or less to about 2.5 or more dry weight percent, preferably not more than 1.5, more preferably about 1.0 dry weight percent of the composition.

A preferred embodiment or the present invention includes the following componenets in the amounts indicated.

TABLE 1

| Component | Approximate Amount |
| --- | --- |
| Active | 50–85 |
| carboxymethylcellulose | 1–5 |
| Additional binders/disintegrants | 10–45 |
| Lubricant | 0.1–3.0 |

The amounts shown in Table 1 are in parts per 100 parts on a dry bases of the granular composition.

The best embodiment composition of the invention contemplated at the time of executing this patent application is as follows, wherein the amount given are in parts per 100 parts by weight on a dry bases of the granular composition.

TABLE 2

| Component | Approximate Amount |
| --- | --- |
| Ibuprofen | 63.0 |
| Na carboxymethyl-cellulose | 3.0 |
| Pregelatinized starch | 17.4 |
| Microcrystalline cellulose | 15.0 |
| Lubricant | 1.0 |
| Povidone | 0.5 |
| Preservative | 0.1 |

In general, the just mentioned composition can be repeatedly formed into tablets having a hardness of 5 kp or more and having a disintegration rate of 5 minutes or less.

In use, the granular compositions of the present invention advantageously may be built to include other active ingredients and/or other excipients. The additional substances may be added either prior to compositing the components to form the granular composition or after the composition is formed (e.g., by dry blending the built granules with such ingredients). Thereafter, the composition may be directly compressed into tablets having eminently suitable values of hardness and disintegration rates for a variety of end use applications including the formation of tablets and capsules.

The compositions of the present invention are preferably made by the method mentioned above, which includes the use of a fluidized bed granulator-dryer. A suitable sized fluidized bed granulator-dryer is charged with ibuprofen and a portion of the cellulosic disintegrant. The amount of cellulosic material added is from about 1 to about 5 percent by weight based on the total weight of the composition. Preferably, about 1.5 percent of the cellulosic material is charged to the fluidized bed. The substances added to the granulator-dryer initially are fluidized until they are thoroughly blended. A second portion of the cellulosics is dispersed in water to yield a slurry of between about 5 and about 15 weight percent solids, using a high sheer mixer. Other components, if desired, may be added either to the dry blend or to the slurry, as needed. The resulting dispersion is then sprayed onto the fluidized bed of ibuprofen and the cellulosic material at a rate sufficient to maintain a bed moisture between about 5 and 20 weight percent and preferably between about 10 and about 16 percent by weight. After complete addition of the dispersion to the fluid bed, the fluidization is continued until the bed moisture has been reduced to about 2 to about 5 percent. The fluidization is then halted. After the fluidization is terminated, the material is sized to the desired proportionate dimensions by using suitable equipment such as a Glatt Quick Sieve ™ or Stoke's Granulator ™. A lubricant is blended with the suitably sized granules using a suitable blending device, such as a double-cone blender which is preferred.

The fluidized bed granulator-dryer may be operated under the following conditions: a stream of heated air is introduced from the bottom of the fluid bed at a sufficient velocity and force to fluidize the powder bed of ibuprofen and cellulosic disintegrant and at a temperature sufficient to heat the powder bed to between about 20° C. and about 50° C. The air velocity, inlet air temperature and the powder bed temperature are dependent on the batch size, dew point of air, and spray rate of the binder solution during the granulatio phase and therefore are adjusted accordingly. The particle size of the bed material is influenced by the atomization pressure used to spray the granulating dispersion, as well as by the moisture level of the fluid bed during the granulation stage. By adjusting operating parameters, the desired particle size and size distribution of the granules can be obtained. If needed, further sizing of the dry granules to obtain a narrow particle size distribution may be achieved by using a Glatt Quick Sieve or other suitable sizing equipment. The built granules preferably will have a particle size of about 140-225 microns.

The term "direct tableting" and terms of like import, as used herein, means that the composition can be formed into a tablet using conventional tablet-forming apparatus and processes without the need for addition of any adjuvant material to the composition. As used herein the term "kp" means kilo ponds, a well known unit of force for expressing hardness or crushing strength of pharmaceutical tablets, when such hardness is determined on a Schleuniger Tablet Hardness Tester.

The following examples and tables illustrate the invention. As used herein, the following terms have the meanings indicated:

(a) "Disintegration time" means the time measured using the disintegration time test method set forth in U.S. Pharmacoepia (hereinafter "USP") XXI for uncoated tablets except that the disks are not employed;

(b) "Dissolution time" means the time measured using the dissolution time test method set forth in USP XXI for ibuprofen tablets;

(c) "Hardness" means the hardness measured on a Schleuniger Tablet Hardness Tester;

(d) "Maximum hardness" means the maximum hardness in which the tablets are substantially free of lamination;

(e) "Friability" means the friability measured on a Roche Friabulator for 20 tablets and 100 revolutions.

Unless othewise indicated, all tablet hardness values are averages for 10 tablets and all tablet weights are averages obtained by weighing 20 tablets as a whole and then dividing by 20. Further, unless otherwise indicated, tablet disintegration times were measured for tablets having about 9 kp hardness.

EXAMPLE 1

Using the procedure described above, a directly tabletable granular composition was prepared in a fluid bed granulator-dryer (Aeromatic, Inc. Model STREA-1) from the following components given on a dry weight percent basis.

TABLE 3

| components | Approximate Amounts, % |
|---|---|
| Ibuprofen | 55.5 |
| Povidone K-90 USP | 0.5 |
| Pregelatinized Starch USP | 3.5 |
| Na carboxymethylcellulose | 3.0 |
| Corn starch | 18.0 |
| Calcium hydrogen phosphate | 19.0 |
| Magnesium stearate | 0.5 |

The batch size exclusive of added water was 1.0 kg. The composition was dried to a final moisture content of 2.4 percent.

The granular composition was directly formed into tablets of 9.5 mm diameter, which had the physical properties as set forth in Table 4 below.

TABLE 4

| Properties | Values |
|---|---|
| Tablet weight | 361 mg |
| Tablet hardness | 12.8 kp |
| Maximum hardness | 18.3 kp |
| Tablet disintegration time | 2 min. 20 sec. |
| Tablet dissolution time (T 80) | <10 min |
| Tablet friability | 0.4% |

EXAMPLE 2

Using the procedure described above, a directly tabletable granular composition was prepared as in Example 1 from the following components given on a dry weight percent basis.

TABLE 5

| Components | Approximate Amounts |
|---|---|
| Ibuprofen | 55.5 |
| Pregelatinized starch USP | 18.0 |
| Calcium hydrogen phosphate | 24.0 |
| Na carboxymethylcellulose | 1.8 |
| Magnesium stearate | 0.5 |
| Methyl paraben | 0.16 |
| Propyl paraben | 0.04 |

The batch size exclusive of added water was 1.0 kg. The composition was dried to a final moisture content of 3.1 percent.

The granular composition was directly formed into ablets of 9.5 mm diameter, which had the physical roperties set forth in Table 6 below.

TABLE 6

| Properties | Values |
|---|---|
| Tablet weight | 364 mg |
| Tablet hardness | 11.8 kp |
| Maximum hardness | 16.3 kp |
| Tablet disintegration time | 2.8-3.2 min |
| Tablet dissolution time (T 80) | <10 min |
| Tablet friability | 0.4% |

EXAMPLE 3

Using the procedure described above, a directly tabletable granular composition was prepared in a fluidized bed granulator-dryer (Glatt Air Technique, Inc.) from the following components given on a dry weight percent basis.

TABLE 7

| Charge to Fluid Bed | |
| --- | --- |
| Ibuprofen | 63 |
| Pregelatinized starch NF | 13.88 |
| Microcrystalline cellulose | 10 |
| Na carboxymethylcellulose | 1.5 |
| Dispersion | |
| Methyl paraben | 0.1 |
| Propyl paraben | 0.02 |
| Povidone (PVP K-90) USP | 0.5 |
| Pregelatinized starch NF | 3.5 |
| Charge to Blender | |
| Stearic acid NF | 0.5 |
| Ca stearate NF | 0.5 |
| Na carboxymethylcellulose | 1.5 |
| Microcrystalline cellulose | 5.0 |

The batch size exclusive of added water was 452.1 kg. The composition was dried to a final moisture content of 2.8 percent and had a density of 0.51 g/cc. The granular composition was sized to the following particle size distribution using a Glatt Quick Sieve.

TABLE 8

| Mesh | Cum % Retained |
| --- | --- |
| +20 | 7 |
| +60 | 49 |
| +100 | 69 |
| +200 | 89 |
| −200 | 100 |

The granular composition was directly formed into tablets of 10.3 mm diameter, which had the tablet physical properties as setforth in Table 9 below.

TABLE 9

| Properties | Values |
| --- | --- |
| Tablet weight | 324 mg |
| Tablet hardness | 6.6 kp |
| Maximum hardness | 6.6 kp |
| Tablet disintegration time | 2 min |
| Tablet dissolution time (T 80) | <10 min |
| Tablet friability | 0.5% |

EXAMPLE 4

In this example the same ingredients in the same proportions as used to form the tablets of Example 3 were physically mixed together without being subjected to the process of the present invention using the fluidized bed technique. It was found that the physical blend could not be tableted because of the poor flow characteristics.

EXAMPLE 5

In this example the procedure described in Example IV of U.S. Patent 4,661,521 was followed except that instead of using acetaminophen as the active ingredient, ibuprofen was used. It was found that tablets made from the ibuprofen-containing granules had inferior dissolution and disintegration characteristics as compared to tablets made from the acetaminophen-containing granules. Furthermore, tablet lubrication is very poor with the ibuprofen granules.

It is understood that the foregoing detailed description is given merely by way of illustration and that many modifications may be made therein without departing from the spirit or scope of the present invention.

What is claimed is:

1. A free flowing particulate ibuprofen-containing granular composition capable of being directly molded into a pharmaceutically acceptable tablet having high hardness, short disintegration time and fast dissolution rate comprising as components thereof:
   (a) from about 50 to about 85 percent, based on the dry weight of the composition, of ibuprofen;
   (b) from about 1 to about 5 percent based on the dry weight of the composition, of an internally cross-linked alkali carboxymethylcellulose;
   (c) a pharmaceutically acceptable lubricant in an amount of at least sufficient to impart effective mold release properties to the tablet;
   (d) cellulose and starch binders and disintegrants; and
   (e) water,
   said composition having been prepared in a fluidized bed granulator-dryer by a process which comprises spraying an aqueous dispersion of a starch binder onto a fluidized powder comprising ibuprofen and a portion of the said carboxymethylcellulose, drying the resulting granules to a moisture level of from about 1 to about 5 percent based on the total weight of the composition; and thereafter blending a lubricant and the remaining portion of the said carboxymethylcellulose with the dry granules.

2. A tablet shaped from the composition of claim 3.

3. The composition of claim 3 wherein the blending is carried out using a double-cone blender.

4. The composition of claim 3 wherein the lubricant is calcium stearate and comprises about 0.1 to 3.0 percent based on the dry weight of the composition.

5. The composition of claim 7 wherein the aqueous spray contains a second pharmaceutically acceptable compressibility-promoting binder in an amount effective for further increasing the obtainable hardness of tablets formed from such composition.

6. The composition of claim 8 wherein the second binder is povidone.

7. The composition of claim 1 wherein the initially fluidized powder contains a second pharmaceutically acceptable compressiiility-promoting binder in an amount effective for further increasing the hardness of tablets formed from such composition.

8. The composition of claim 10 wherein the second binder is pregelatinized starch.

9. A method of building free-flowing particulate ibuprofen-containing granules capable of being directly molded into a pharmaceutically acceptable tablet having high hardness, short disintegration time, and fast dissolution rate comprising:
   (a) fluidizing a finely divided powder of ibuprofen and an internally cross-linked alkali carboxymethylcellulose, each component having a particle size of about 15 to about 60 microns;
   (b) during the fluidization, spraying the fluidized powder with an aqueous dispersion of a pharmaceutically acceptable compressiblilty-promoting binder in an amount effective for increasing the obtainable hardness of tablets made from the resulting composition;
   (c) ceasing the spraying;
   (d) continuing the fluidization until the thus-built granules have a moisture content of about 2.0 to 5.0 weight percent water based on the total weight of the composition;
   (e) ceasing the fluidization; and
   (f) blending the dried granules with a pharmaceutically acceptable lubricant in an amount at least sufficient to impart effective mold release properties to tablets made from the resulting granules and with additional carboxymethylcellulose, whereby free-flowing granules having a particle size of about 140-225 microns are produced and being capable of being directly formed into pharmaceutically acceptable tablets.

10. The process of claim 9 wherein the blending is carried out using a double-cone blender.

11. The process of claim 9 wherein the lubricant is stearic acid and comprises about 0.1 to 3.0 percent based on the dry weight of the granules.

12. The process of claim 9 wherein the lubricant is calcium stearate and comprises aboiut 0.1 to 3.0 percent based on the dry weight of the granules.

13. The process of claim 1 the aqueous spray dispersion contains a second pharmaceutically acceptable compressibility-promoting binder in an amount effective for further increasing the obtainable hardness of tablets formed from the granules.

14. The process of claim 1 wherein the second binder is povidone.

15. The process of claim 9 wherein both the initially fluidized powder contains a second pharmaceutically acceptable compressibility-promoting binder in an amount effective for increasing the hardness of tablets formed from the granules.

16. The process of claim 13 wherein the second binder is pregelatinized starch.

17. The process of claim 9 wherein a preservative is adddded during the spra\`ing step in an amount sufficient to minimize microbial contamination of tablets made from the granules.

18. The process of claim 17 wherein the preservative is a lower alkyl ester of parahydroxybenzoic acid.

19. The process of claim 18 where in the alkyl moeity of the preservative is $C_1$-$C_5$ alkyl.

20. A method of building a free-flowing particulate ibuprofen-containing granules capable of being directly molded into a pharmaceutially acceptable tablet having high hardness, short disintegration time, and fast dissolution rate comprising:
    (a) fluidizing a dry finely divided powder of ibuprofen together with a pharmaceutically acceptable binder composed of a mixture on internally cross-linked sodium carboxymethylcellulose, pregelatinized starch and microcrystalline cellulose, each ingredient of which having a particle size of about 15 to about 60 microns.
    (b) during the fluidization, spraying the fluidized powder with an aqueous dispersion containing a pharmaceutically acceptable binder composed of a mixture of pregelatinized starch and povidone and a lower alkyl ester of parahydroxybenzoic acid as a pharmaceutically acceptable preservative;
    (c) ceasing the spraying;
    (d) continuing the fluidization until the intermediate built granules have a moisture content of about 2.0 to about 5.0 weight percent water based on the total weight of the composition;
    (e) ceasing the fluidization;
    (f) blending the intermediate built granules with a lubricant, additional internally cross-linked sodium carboxymethylcellulose and microcrystalline cellulose as a mixture of binders;
    (g) the binders present in the intially fluidized powder and the aqueous dispersion and added during blending being present in an amount effective for increasing the obtainable hardness of tablets molded from the ultimate granules;
    (h) the lubricant being present in an amount sufficient to impart effective mold release properties to tablets molded from the ultimate granules;
    (i) the preservative being present in an amount sufficient to minimize microbial contamination of tablets molded from the ultimate granules;
    whereby free-flowing granules having a particle size of about 140-225 microns are built and being capable of directly molded into pharmaceutically acceptable tablets with an ibuprofen dosage of about 100 to about 300 mg.

21. The process of claim 20 wherein the internally cross-linked sodium carboxymethylcellulose composes about 3 weight percent of the ultimate granules and having been incorporated in the initially fluidized powder and in the composition added during blending in approximately equal amounts.

22. The process of claim 22, wherein the ultimate granules on a dry basis comprises about 63% ibuprofen, about 17% pregelatinized starch, about 15% microcrystalline cellulose, 3% internally corss-linked sodium carboxymethylcellulose, about 1% lubricant, about 0.5% povidone and about 0.1% lower alkyl ester of parahydroxybenzoic acid.

23. The process of claim 22 wherein the ester of parahydroxybenzoic acid is a mixture of methyl and ethyl esters.

24. The composition of claim 3 wherein the lubricant is stearic acid and comprises about 0.1 to 3.0 percent based on the dry weight of the composition.

25. The composition of claim 3 wherein the lubricant is a mixture of stearic acid and calcium stearate.

* * * * *